United States Patent [19]

Keller et al.

[11] Patent Number: 5,055,821
[45] Date of Patent: Oct. 8, 1991

[54] SYSTEM FOR TRANSMITTING DATA BETWEEN A ROTATING PART AND A STATIONARY PART

[75] Inventors: Walter Keller, Erlangen; Fritz Peter, Spardorf, both of Fed. Rep. of Germany

[73] Assignee: Siemens Aktiengesellschaft, Munich, Fed. Rep. of Germany

[21] Appl. No.: 462,236

[22] Filed: Jan. 9, 1990

[30] Foreign Application Priority Data

Feb. 6, 1989 [EP] European Pat. Off. ........ 89102031.5

[51] Int. Cl.$^5$ .............................................. G08B 1/08
[52] U.S. Cl. .................................. 340/286.01; 378/15
[58] Field of Search ............... 378/10, 15; 340/286.01, 340/442, 425.5; 439/5, 18, 24, 29

[56] References Cited

U.S. PATENT DOCUMENTS

| 3,095,252 | 6/1963 | Adkins . | |
|---|---|---|---|
| 3,297,984 | 1/1967 | Necker | 340/442 |
| 4,063,792 | 12/1977 | Lodge | 439/5 |
| 4,153,842 | 5/1979 | Rohmfeld | 378/10 X |
| 4,181,850 | 1/1980 | Fairbairn . | |
| 4,201,430 | 5/1980 | Dinwiddie et al. | 439/24 |
| 4,219,733 | 8/1980 | Tschunt | 378/10 |
| 4,236,079 | 11/1980 | Sandland . | |
| 4,310,826 | 1/1982 | D'Angiolillo | 340/442 |

FOREIGN PATENT DOCUMENTS 2026812 2/1980 United Kingdom .................. 378/15

Primary Examiner—Joseph A. Orsino
Assistant Examiner—Brian R. Tumm
Attorney, Agent, or Firm—Hill, Van Santen, Steadman & Simpson

[57] ABSTRACT

A system for transmitting data between a rotating part and a stationary part, such as is suitable for use in a computer tomography apparatus, has a wiper ring assembly and a number of electronic components disposed on the rotating part from which data is to be transmitted with a minimum of disturbance to the stationary part. A common power supply is provided on one of the stationary part or the rotating part, which powers all components. This common power supply is connected to the components on the other part via a further wiper ring assembly, or via further wiper ring assemblies.

1 Claim, 2 Drawing Sheets

SYSTEM FOR TRANSMITTING DATA BETWEEN A ROTATING PART AND A STATIONARY PART

BACKGROUND OF THE INVENTION

1. Field of the Invention

The present invention is directed to a system for transmitting data between a rotating part and a stationary part, and in particular to such a system making use of one or more wiper ring assemblies for transmitting data between electronic components.

2. Description of the Prior Art

Data transmission systems for transmitting data between a rotating part and stationary part are used, for example, in computer tomography devices for transmitting detector data from the live ring, on which the radiation detector is disposed, to signal processing and computer circuitry mounted either on the stationary part, or at a remote stationary location. If the power supply to the x-ray source, which is also disposed on the live ring together with the detector, is also transmitted via wiper rings, a continuous rotation of the measuring unit, consisting of the x-ray source and the radiation detector, can be achieved, and thus an extremely rapid scanning of a plurality of parallel slices of the exposure subject is possible.

SUMMARY OF THE INVENTION

It is an object of the present invention to provide a data transmission system for transmitting data between a rotating part and a stationary part wherein disruption-free data transmission is assured, so that the data transmission means can be used in a computer tomography apparatus for the transmission of detector data.

This object is achieved in accordance with the principles of the present invention in a data transmission system wherein a common power supply for all of the electronic components is provided on one part, and is connected to the components of the other part via a wiper ring arrangement. In the data transmission system disclosed herein, all electronic components on the rotating part and on the stationary part are supplied with power from a common power supply. Disturbance free data transmission is thus assured.

DESCRIPTION OF THE PREFERRED EMBODIMENTS

Figure 1:
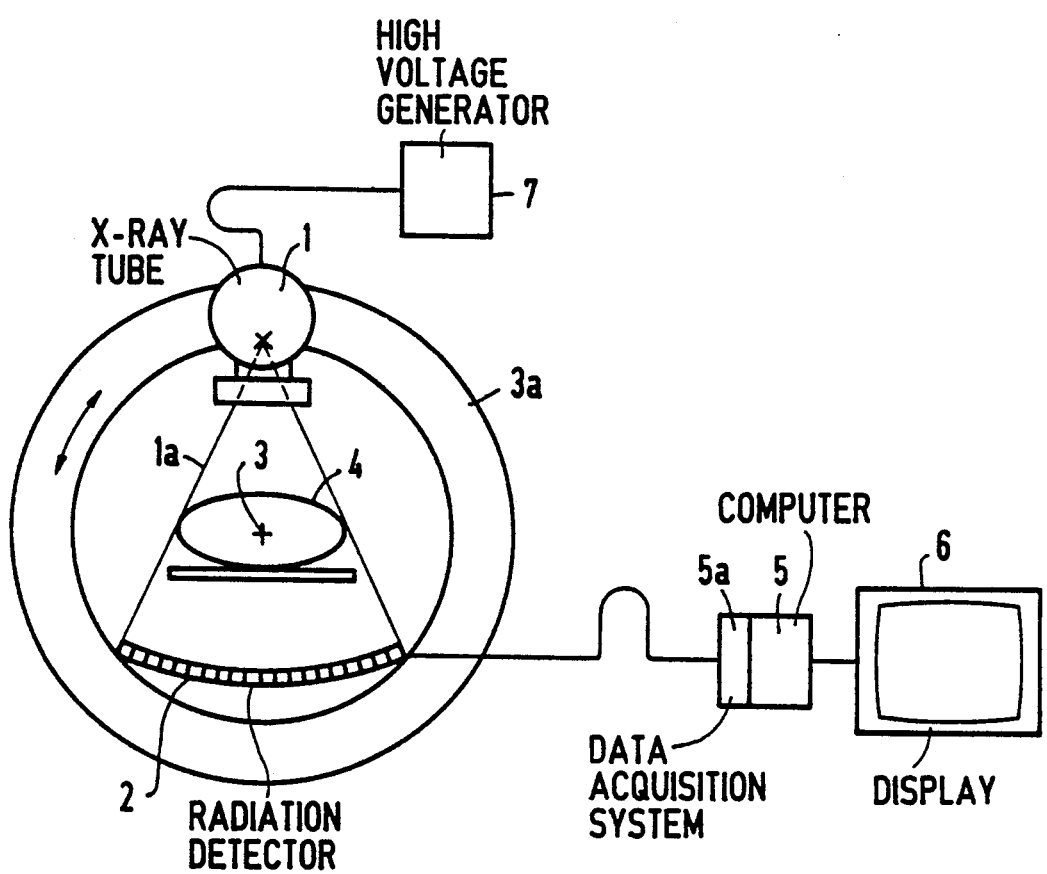
FIG. 1 is a schematic block diagram of a computer tomography apparatus of the type in which the data transmission system disclosed herein can be employed.

A conventional computer tomography apparatus is shown in FIG. 1 having an x-ray tube 1 as the radiation source, and a radiation detector 2 which may have over one hundred, for example 512, individual detectors arranged in a row. The x-ray tube 1 is fed by a high voltage supply 7 via a wiper ring assembly (not shown in FIG. 1). The x-ray tube 1 emits a fan-shaped x-ray beam 1a having a cross-sectional extent perpendicular to the slice plane under examination which is equal to the slice thickness, and which is of such a size in the slice plane that the entire exposure subject is penetrated by radiation.

The radiation detector 2 is curved around the focus of the x-ray tube 1. The measuring arrangement consisting of the x-ray tube 1 and the detector arrangement 2 is rotatable around an axis 3 by a rotating frame or live ring 3a. The axis 3 substantially coincides with the longitudinal axis of an examination subject 4. The number of detectors of the radiation detector 2 is selected to correspond to the desired image resolution. The radiation attenuated by the examination subject 4 is incident on the detectors of the radiation detector 2, each of which generates an electrical signal corresponding to the radiation incident thereon. These values are used to construct a pixel matrix of the transirradiated transverse slice of the examination subject 4 in a computer 5, based on the rotation of the measuring arrangement. The image constructed by the computer 5 is reproduced on a display 6.

As is known, each detector element of the radiation detector 2 has an associated measuring channel which leads to the computer 5. Each channel includes amplifier circuits, multiplexers and analog-to-digital converters, which in combination form a data acquisition system 5a.

A rapid scanning of a plurality of parallel slices of the examination subject 4 is possible if the rotating frame 3a can continuously rotate, with the support for the examination subject 4 being advanced through the interior of the rotating frame 3a. To this end, the x-ray tube 1 is supplied with power from the high voltage generator 7 via a wiper ring assembly (not shown) and the data from the detector elements of the radiation detector 2 are transmitted to the data acquisition system 5a via a further wiper ring assembly, or via a plurality of wiper ring assemblies.

Figure 2:
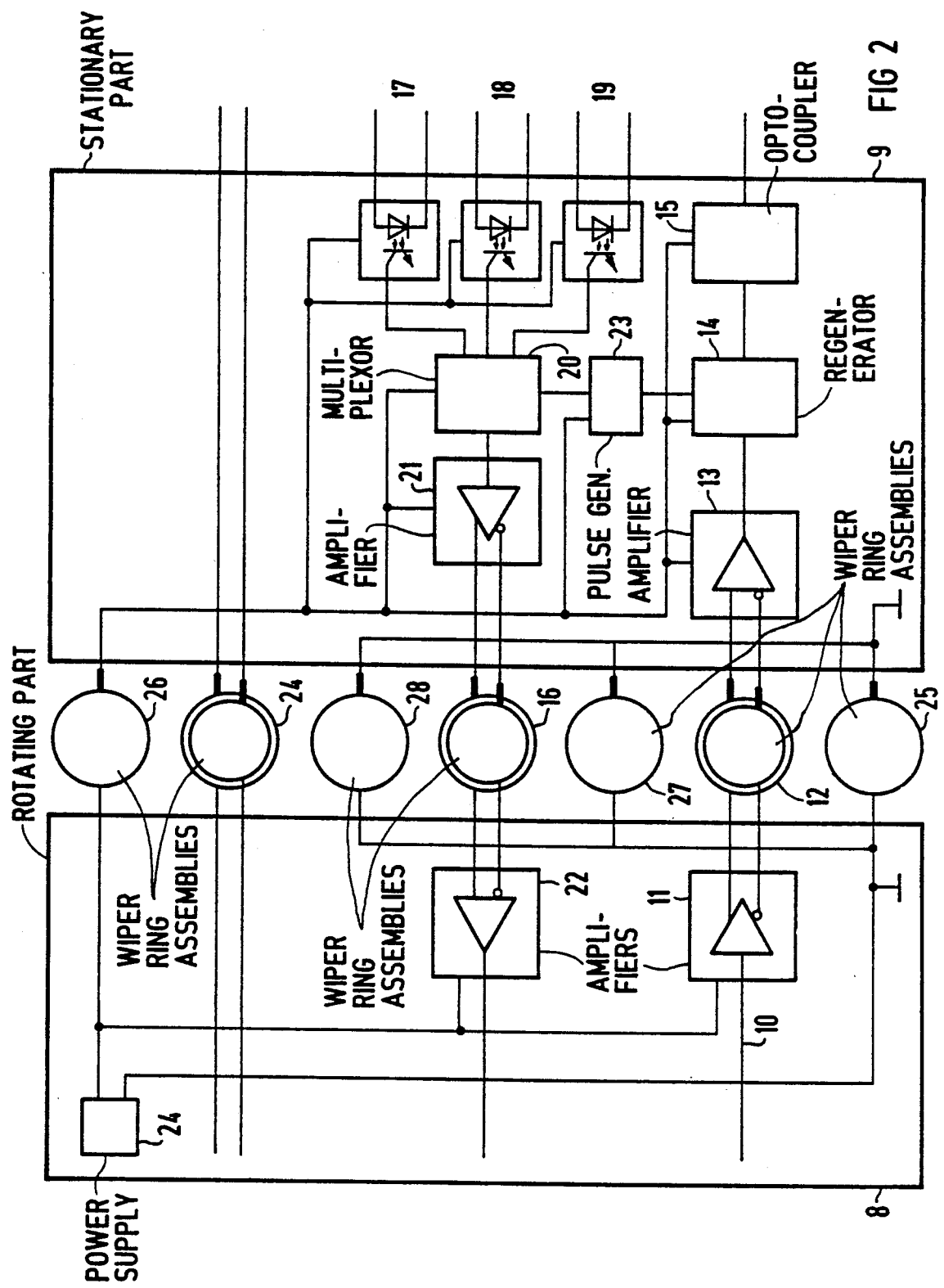
FIG. 2 is a schematic block circuit diagram of the data transmission system constructed in accordance with the principles of the present invention.

In the data transmission system shown in FIG. 2, the rotating part is schematically referenced 8 and the stationary part is schematically referenced 9. The data from the radiation detector 2 arrive on a line 10 and are transmitted via an amplifier 11 and a wiper ring assembly 12 to an amplifier 13 in the stationary part 9. A regenerator or repeater 14 and an opto-coupler 15 follow the amplifier 13. A further wiper ring assembly 16 serves the purpose of transmitting control signals to inputs 17, 18 and 19. The wiper ring assembly 16 is preceded by a multiplexer 20 and by an amplifier 21, and is followed by an amplifier 22. A pulse generator 23 synchronizes the operation of the multiplexer 20 and the regenerator 14. Further opto-couplers are disposed between the inputs 17, 18 and 19 and the multiplexer 20. The power to the x-ray tube 1 is transmitted via a wiper ring assembly 24.

The power supply for the components 11 and 22 on the rotating part and the components 13, 14, 15, 20, 21 and 23 on the stationary part 9 is undertaken by a common power supply unit 24 on the rotating part 8. Wiper ring assemblies 25, 26, 27 and 28 are provided for transmitting current from the power supply unit 24 to each of the components 13, 14, 15, 20, 21 and 23 on the stationary part 9. All components of the rotating part 8 and of the stationary part 9 are thus supplied by the power supply unit 24. As a result, an optimum, disturbance-free transmission of data is assured.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an apparatus having a rotating part and a stationary part, a data transmission system for transmitting data between said stationary part and said rotating part comprising:
- a first plurality of electronic components on said rotating part, said first plurality of electronic components requiring power to operate and generating a data stream;
- a second plurality of electronic components on said stationary part, said second plurality of electronic components requiring power to operate and processing said data stream from said first plurality of electronic components;
- a common power supply means for supplying power to all of said components on said stationary part and said rotating part, said common power supply means being disposed on said rotating part and being directly connected to the electronic components on said rotating part and connected to the electronic components on the stationary part via a first wiper ring assembly; and
- a second wiper ring assembly electrically connected between said first and said second pluralities of electronic components for transmitting said data stream from said first plurality of electronic components to said second plurality of electronic components.

* * * * *